(12) United States Patent
Kondo et al.

(10) Patent No.: US 8,712,204 B2
(45) Date of Patent: Apr. 29, 2014

(54) OPTICAL MODULATION ELEMENT

(71) Applicant: NGK Insulators, Ltd., Nagoya (JP)

(72) Inventors: Jungo Kondo, Miyoshi (JP); Yuichi Iwata, Nagoya (JP); Tetsuya Ejiri, Kasugai (JP)

(73) Assignee: NGK Insulators, Ltd., Aichi-prefecture (JP)

( * ) Notice: Subject to any disclaimer, the term of this patent is extended or adjusted under 35 U.S.C. 154(b) by 0 days.

(21) Appl. No.: 14/021,148

(22) Filed: Sep. 9, 2013

(65) Prior Publication Data
US 2014/0010493 A1     Jan. 9, 2014

Related U.S. Application Data

(63) Continuation of application No. PCT/JP2012/057666, filed on Mar. 16, 2012.

(30) Foreign Application Priority Data

Mar. 17, 2011    (JP) ................................. 2011-058732

(51) Int. Cl.
    *G02B 6/10*          (2006.01)
    *G02F 1/295*        (2006.01)

(52) U.S. Cl.
    USPC ............................................. 385/132; 385/8

(58) Field of Classification Search
    CPC .................................. G02B 6/10; G02F 1/295
    USPC ...................................................... 385/8, 132
    See application file for complete search history.

(56) References Cited

U.S. PATENT DOCUMENTS 4,866,406 A      9/1989    Minakata et al.
(Continued)

FOREIGN PATENT DOCUMENTS

JP               63-49732 A       3/1988
(Continued)

OTHER PUBLICATIONS

Deka, C., et al., "Time-resolved fluorescence-decay measurement and analysis on single cells by flow cytometry," Appl. Optics 1996;35(22):4481-4489.

(Continued)

*Primary Examiner* — Charlie Peng
(74) *Attorney, Agent, or Firm* — Cermak Nakajima LLP; Tomoko Nakajima

(57) ABSTRACT

An optical modulation device 1 includes a supporting body 2 including a pair of grooves 2b, 2c and a protrusion 2d between the grooves, a ridge par 6 including a channel type optical waveguide capable of multi mode propagation, a first side plate part 3A formed in a first side of the ridge part 6, a second side plate part 3B formed in a second side of the ridge part, a first adhesive layer 4A adhering the first side plate part 3A and the supporting body 2, a second adhesive layer 4B adhering the second side plate part 3B and the supporting body 2, and a third adhesive layer 4C adhering the ridge part 6 and the protrusion 2d. The device 1 further includes a first electrode 7A provided on a side face 6b of the ridge part on the first groove side, and a side face 3b and an upper face 3c of the first side plate part, and a second electrode 7B provided on a side face 6c of the ridge part 6 in the second groove side, the second groove 2c and a side face 3b and an upper face 3c of the second side plate part 3B. The first electrode 7A and the second electrode 7B apply a modulation voltage modulating light propagating in the channel type optical waveguide.

4 Claims, 2 Drawing Sheets

(56) References Cited

U.S. PATENT DOCUMENTS

| | | | |
|---|---|---|---|
| 5,106,211 A * | 4/1992 | Chiang et al. | 385/132 |
| 5,825,047 A | 10/1998 | Ajisawa et al. | |
| 6,798,552 B2 * | 9/2004 | Tada | 359/248 |
| 8,582,927 B1 * | 11/2013 | Thaniyavarn | 385/2 |
| 2001/0055453 A1 | 12/2001 | Mizuuchi et al. | |
| 2003/0012540 A1 | 1/2003 | Kato et al. | |
| 2004/0258348 A1 * | 12/2004 | Deliwala | 385/14 |
| 2009/0190880 A1 * | 7/2009 | Hikita et al. | 385/14 |

FOREIGN PATENT DOCUMENTS

| | | |
|---|---|---|
| JP | 01-302325 A | 12/1989 |
| JP | 3-198025 A | 8/1991 |
| JP | 2002-250949 A | 9/2002 |
| JP | 2002-372641 A | 12/2002 |
| JP | 2005-221894 A | 8/2005 |
| JP | 2009-122183 A | 6/2009 |

OTHER PUBLICATIONS

International Search Report for PCT Patent App. No. PCT/JP2012/057666 (Jul. 3, 2012).

Written Opinion for PCT Patent App. No. PCT/JP2012/057666 (Jul. 3, 2012).

* cited by examiner

OPTICAL MODULATION ELEMENT

FIELD OF THE INVENTION

The present invention relates to optical modulation devices suitable for a light source for flow cytometry.

BACKGROUND ARTS

It has been intensively developed a product of testing or processing system utilizing laser in fields of bio cell analysis and processing. Flow cytometry may be listed as one example. Flow cytometry is a technique of dispersing cells in living bodies in fluid, of flowing the fluid as a narrow flow and of optically analyzing the individual cells. A system for use in flow cytometry is called flow cytometers.

A flow cytometer irradiates laser light onto cells, and then detects forward scatter (abbreviated as FSC) in a direction slightly shifted from the rays (it would be saturated with strong light from a light source on the same axis as the light) and side scatter (SSC) in a direction perpendicular to the light. Further, the cells are labeled with a fluorescence material and fluorescence generated by the laser light is detected. In the case of cells, the size of the cells can be analyzed by FSC and the complexity within the cells (derived from shape of the nuclei, organelles, film structure or the like) can be analyzed by SSC. Thanks to combination of detectors, fluorescence materials and immunostaining, various kinds of analysis can be made. It has recently supplied a system utilizing a plurality of lights and detectors (4 kinds of lights, 14 kinds of detectors or the like), and a plurality of antibodies may be used to perform more sophisticated analysis at the same time. It has been further supplied a system including a cell sorter as a standard equipment, so that target particles can be taken at a high precision and high speed by switching flow routes in a sheath. Maximum of 4 kinds of populations can be separated out using a commercial system, and it is possible, in theory, to process 90000 particles per one second.

As a laser, it has been used a large gas laser of water cooled type requiring complicated operation in prior arts. Thanks to development of laser technology and a flow cell detection system of high sensitivity, it is mainly used air cooled type laser which is compact, simple and has a long life. It has been specifically used air cooled type argon laser (488 nm), air cooled type helium-neon laser (633 nm), air cooled type helium-cadmium laser (325 nm) or the like. More recently, it has been used a semiconductor laser or a solid state laser (light-excited semiconductor laser), utilizing a wavelength conversion device, which are more compact and consume a less electric power.

According to flow cytometers, laser light may be transmitted through an optical fiber until it is irradiated into fluid. The optical intensities of the used laser may exceed several tens to a hundred mW, so that a total of the intensities at all the wavelengths may be 300 mW or higher. Further, the spot size is as large as several tens μm or more, so that it is used a multi-mode fiber of several tens μm or larger as the optical fiber. In this case, it is required that the spot shape of the laser light is stable and not deviated for accurately measuring the individual cells. Therefore, for stabilizing the spot shape or optical intensity of the laser light, it may be used an optical regulation device for modulating the intensity or phase.

As an optical modulation device utilizing a ridge type optical waveguide, Japanese Patent Publication Nos. 2002-250949A, 2005-221894A and S63-049732A were flied, for example.

According an optical modulation device in Japanese Patent Publication No. 2002-250949A, a ridge type optical waveguide is adhered to a supporting body.

An optical modulation device according to Japanese Patent Publication No. 2005-221894A is made of a material exhibiting secondary non-linear optical effects. It is further included a first step of adhering a first substrate 21 having a periodic domain inversion structure and a second substrate 22 by diffusion adhesion through thermal treatment, a second step of polishing the first substrate 21 into a predetermined thickness for forming the optical waveguide therein, and a third step of adhering the first substrate 21 to a third substrate 23 by diffusion adhesion through thermal treatment. Further, as the ridge type waveguide, it is disclosed the structure of grinding parts of the first, second and third substrates.

According to an optical modulation device described in Japanese Patent Publication No. S63-049732A, a ridge type optical waveguide is formed on an x-cut LN substrate, belonging to an electro-optic material, and electrodes are formed on the side faces.

Besides, as a measure against drift of an optical modulator, it is described to use an $SiO_2$ buffer layer in Japanese Patent No. 1789177B.

SUMMARY OF THE INVENTION

It is known a prior modulation device of providing a pair of modulation electrodes on both side faces of the ridge part and applying a modulating voltage on light propagating within the ridge part through the pair of modulation electrodes, as described in Japanese Patent Publication No. S63-049732A. In the course of developing an optical modulation device for use for example, in flow cytometry, the inventors have tried to utilize an optical waveguide structure as described in Japanese Patent Publication No. 2002-250949A and to form the modulation electrodes, respectively, on both side faces of the ridge part as described in Japanese Patent Publication No. S63-049732A.

As a result, however, it has been proved that a driving voltage required for the optical modulation (half wavelength voltage) is considerably deviated over time to make the device unpractical.

In the case that an optical modulation device is used in the field of flow cytometry, for example, the power intensity of the laser light becomes as large as 300 mW or more, for example. Further, it is required laser of a short wavelength in many cases and the wavelength may be 700 nm or shorter, for example. As the optical intensity was increased or the wavelength was made shorter as such, the deviation of the driving voltage became considerably larger.

An object of the present invention is, in an optical modulation device of applying modulation on light propagating within a ridge type optical waveguide, to provide a structure in which damage of the optical waveguide due to heat generation can be prevented and the deviation of driving voltage can be reduced, when an optical intensity is increased or a wavelength of light is shortened.

The present invention provides an optical modulation device including a supporting body having a first groove, a second groove and a protrusion between the grooves, and a ridge part including a channel type optical waveguide formed therein for multi mode propagation and made of an electro-optic material. The device further includes a first side plate part formed in a first side of the ridge part and made of an electro-optic material, a second side plate part formed in a second side of the ridge part and made of an electro-optic material, a first adhesive layer adhering the first side plate part and the supporting body, a second adhesive layer adhering the second side plate part and the supporting body, and a third adhesive layer adhering the ridge part and the protrusion. The device further includes a first electrode provided on a side face of the ridge part in the first groove side, the first groove, a side face of the first side plate part and an upper face of the first side plate part, and a second electrode provided on a side face of the ridge part in the second groove side, the second groove, a side face of the second side plate part and an upper face of the second side plate part. A modulating voltage is applied between the first electrode and second electrode to modulate a phase of light propagating within the channel type optical waveguide.

The inventors studied the cause of the considerable deviation of the driving voltage in the case that the optical intensity is increased or the light wavelength is shortened in the construction of sandwiching the ridge part between a pair of the modulation electrodes as described in Japanese Patent Publication No. S63-049732A. As a result, it was found that the temperature of the ridge part is elevated and the optical propagation characteristic are changed over time and that the state of charges on a surface of the electro-optic crystal substrate is deviated due to pyroelectric effects.

In the case that the temperature is rapidly changed, internal, electrical field due to the surface charges exceeds a threshold value of insulation breakdown to result in the fracture of the waveguide.

Based on the findings, the inventors tried to form the grooves further in the supporting body, and to extend the modulation electrode to a surface of the supporting body facing the groove, to the side face of the side plate part facing the groove and to the upper face of the side plate part, in addition to the side face of the ridge part. By forming the groove, forming the modulation electrode over the whole of the side face of the ridge part and extending it to the groove, the side face and upper face of the side plate part as such, heat generated around the ridge part due to the light propagation is transmitted to facilitate the dissipation of the heat. As a result, it is found that the considerable deviation of the driving voltage can be prevented in the case that the optical intensity is increased or the light wavelength is shortened. The present invention was thus made.

Further, according to the inventive structure, a low refractive index material is positioned under, over, in the right side of and in the left side of the ridge part, resulting in the structure of strong confinement of light and mode pattern with improved symmetry. By these, the mode pattern is stabilized and is not susceptible to change in the case that the wavelength of light is changed.

EMBODIMENTS FOR CARRYING OUT THE INVENTION

Figure 1:
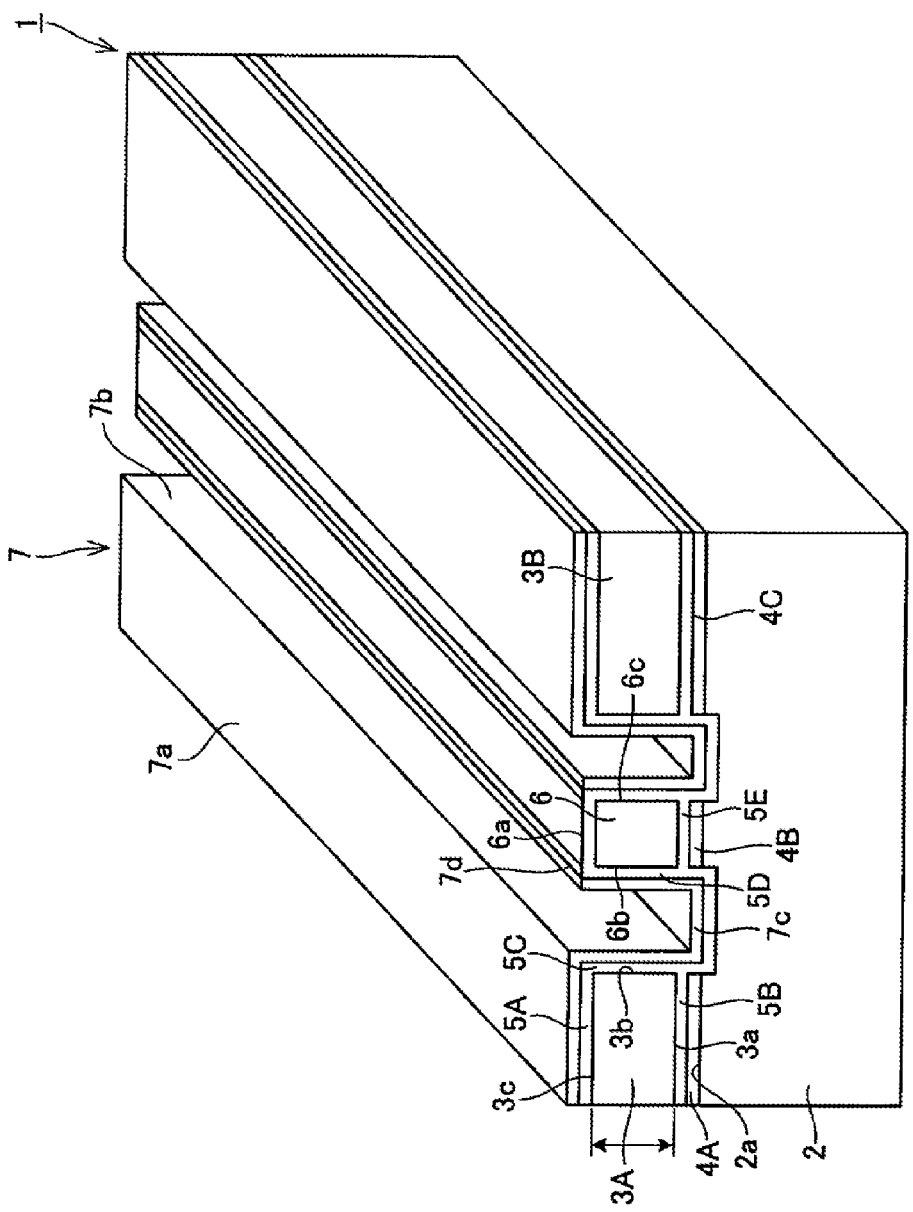
FIG. 1 is a perspective view schematically showing an optical modulation device 1 according to an embodiment of the present invention.

A first groove 2b and a second groove 2c are formed on the side of an upper face 2a of a supporting body 2, and a protrusion 2d is formed between a pair of the grooves 2b and 2c. On the protrusion 2d, a bottom face 6d of a ridge part 6 made of an electro-optic crystal is adhered through a third adhesive layer 4C. 'According to the present example, buffer layers 5D are formed on an upper face 6a, a first side face 6b and a second side face 6c of the ridge part 6, respectively, and a buffer layer 5E is formed on the bottom face 6d of the ridge part 6.

In the outside of the first groove 2b, a bottom face 3a of a first side plate part 3A made of an electro-optic material is adhered onto a surface 2a of a supporting body 2 through a first adhesive layer 4A. According to the present example, a buffer layer 5B is formed on the bottom face 3a of the side plate part 3A, a buffer layer 5C is formed on the side face 3b, and a buffer layer 5A is formed on a upper face 3c. Further, in the outside of the second groove 2c, the bottom face 3a of a second side plate part 3B made of an electro-optic material is adhered onto the surface 2a of the supporting body 2 through a second adhesive layer 4B. According to the present example, a buffer layer 5B is formed on the bottom face 3a of the side plate part 3B, a buffer layer 5C is formed on the side face 3b, and a buffer layer 5A is formed on the upper face 3c.

Then, a first modulating electrode 7A is formed over the upper face 3c and the side face 3b on the side of the ridge groove 8A of the side plate part, the groove 2b and the side face 6b of the ridge part 6. That is, the modulating electrode 7A includes a voltage applying part 7d for applying a voltage onto the ridge part 6, as well as conductive films 7c, 7b and 7a connected to the voltage applying part, and the conductive film 7a is extended to the upper face 3c of the side plate part 3A. Further, a second modulating electrode 7B is formed over the upper face 3c and the side face 3b on the side of the ridge groove 8B of the side plate part 3B, the groove 2c and the side face 6c of the ridge part 6. That is, the modulating electrode 7B includes a voltage applying part 7d for applying a voltage onto the ridge part 6, as well as conductive films 7c, 7b and 7a connected to the voltage applying part, and the conductive film 7a is extended to the upper face 3c of the side plate part 3B.

According to the present invention, light is propagated in multi-mode propagation mode, so that the intensity of the propagating light can be increased. Then, the ridge grooves 8A, 8B for forming the ridge part 6 is deeper than a thickness "Twg" of the substrate and the grooves 2b and 2c reach the supporting body 2. As described, the ridge groove is extended to the supporting body 2 and the modulating electrode is extended over the side face of the ridge part 6, grooves 2a, 2b of the supporting body, and upper faces 2c and side faces 3b of the side plate parts, so that heat generated around the ridge part due to the propagation of light is transmitted and the dissipation of heat is facilitated. As a result, it is possible to reduce the considerable deviation of driving voltage even when the light intensity is increased or wavelength of light is shortened.

According to the present invention, a pair of the grooves 2b and 2c and the protrusion 2d between the grooves are provided in the supporting body 2.

The material of the supporting body includes lithium niobate, lithium tantalate, lithium niobate-lithium tantalate solid solution, lithium potassium niobate, a glass such as quartz glass, quartz, Si or the like.

A process of forming the grooves 2b and 2c in the supporting body is not particularly limited, and includes mechanical processing, ion milling, dry etching, laser ablation or the like.

According to the present invention, light is propagated in a channel type optical waveguide in multi-mode, by adjusting the wavelength of the propagating light and height of the ridge part 6. It is thereby possible to prevent the concentration of light and to propagate light having a relatively large optical intensity. On the viewpoint, the thickness "Twg" of the ridge part 6 may preferably be 25 μm or larger and 150 μm or smaller.

The width "Wr" of the ridge part 6 may preferably be 20 μm to 100 μm and more preferably be 25 μm to 90 μm. Besides, the width "Wr" of the ridge part 6 is a distance between both edge parts of the upper face 6a of the ridge part 6.

Materials of the ridge part, first side plate part and second side plate part include lithium niobate, lithium tantalate, lithium niobate-lithium tantalate solid solution and lithium potassium niobate and may preferably same with each other. Further, doping of MgO or the like may be made and it may be of congruent composition or stoichiometric composition.

A difference of each of refractive indices of the first adhesive layer, second adhesive layer and third adhesive layer and that of the material of the ridge part or the side plate parts may preferably be 10 percent or more, and more preferably be 20 percent or more, of the refractive index of each adhesive layer. Further, the thickness of each adhesive layer may preferably be 0.1 μm or more on the viewpoint of confinement of light and may preferably be 3 μm or smaller, on the viewpoint of reducing the deviation of substrate thickness after it is subjected to grinding and thinning process.

The materials of the first adhesive layer, second adhesive laser and third adhesive layer may be an inorganic adhesive, an organic adhesive or a combination of an inorganic adhesive and an organic adhesive.

Although specific examples of the organic adhesive is not particularly limited, it may be epoxy resin adhesive, a thermosetting resin adhesive, an ultraviolet curable resin adhesive, or "Alon ceramics C" (trade name: Supplied by To a Gosei Co. Ltd.,) having a thermal expansion coefficient (thermal expansion coefficient of $13\times10^{-5}$/K) near that of an electro-optic single crystal such as lithium niobate.

Further, the inorganic adhesive may preferably have a low dielectric constant and an adhesive temperature (working temperature) of about 600° C. or lower. Further, it is preferable that a sufficiently high adhesive strength can be obtained during the processing. Specifically, it may preferably be a glass having a composition of one or plural elements of silicon oxide, lead oxide, aluminum oxide, magnesium oxide, calcium oxide, boron oxide or the like. Further, another inorganic adhesive includes, for example, tantalum pentoxide, titanium oxide, niobium pentoxide and zinc oxide.

The method of forming the inorganic adhesive layer is not particularly limited and includes sputtering, vapor deposition, spin coating, or sol-gel method. Further, a sheet of an adhesive may be interposed to join them. Preferably, a sheet of a resin adhesive of a thermosetting, photo curing or photo thickening resin is interposed between the bottom face of the layer of an electro-optic material and the supporting body 2, and the sheet is then cured. Such sheet may appropriate be a resin film having a thickness of 300 μm or smaller.

According to the present invention, the first electrode is provided on the side face of the ridge part in the side of first groove, the first groove, the side face of the first side plate part and the upper face of the side plate part of the first side plate part, and the second electrode is provided on the side face of the ridge part in the side of the second groove, the second groove, the side face of the second side plate part and upper face of the second side plate part. Here, although it is necessary that the first electrode and second electrode are electrically connected in the inside, respectively, it is not required that the whole of the each face is covered with the electrode, and it is permitted that there is a region which is not party covered by the electrode.

The material of each of the electrodes is not particularly limited as far as desired conductivity can be obtained, and includes gold, silver, copper, aluminum, carbon, molybdenum, for example.

According to a preferred embodiment, it is provided a buffer layer covering the upper face, first side face and second side face of the ridge part, and the buffer layer is provided between the first electrode or second electrode and the ridge part. The buffer layer reduces absorption loss by each electrode, to improve the confinement of light within the ridge part and to realize an optical waveguide having a spot pattern which is excellent in the symmetry as an optical fiber.

For this, a difference between the refractive index of the ridge part 6 and that of the buffer layer may preferably be 10 percent or larger, and more preferably be 20 percent or larger, of the refractive index of the buffer layer. Further, the thickness of the buffer layer may preferably be 0.1 μm or larger on the viewpoint of confinement of light and may preferably be 1 μm or smaller on the viewpoint of increase of a half-wavelength voltage.

The material of the buffer layer may preferably be $SiO_2$ and $Ta_2O_3$.

A value "Tsp" obtained by subtracting the height "Twg" of the ridge part 6 from the depth "Twg+Tsp" of the ridge grooves 8A, 8B may preferably be 20 μm or larger and more preferably be 30 μm or larger, on the viewpoint of preventing the deviation of driving voltage.

Further, a distance "Ws" between the edge of the upper face of the ridge part 6 and edge of the upper face of the side plate part 7A (7B) may preferably be 30 μm or larger, and more preferably be 45 μm or larger, on the viewpoint of preventing the deviation of driving voltage. Further, although the upper limit of Ws is not particularly defined, it may be 300 μm or smaller on the viewpoint of ease of processing.

Further, it is effective for facilitating the heart dissipation to a space in the groove and for reducing the deviation of driving voltage, by satisfying the relationship of (Twg+Tsp)/5≤Ws.

The present invention is particularly effective in the case that the intensity of light propagating in the channel type optical waveguide is 300 mW or larger. The present invention is particularly effective in the case that the wavelength of light propagating in the channel type optical waveguide is 550 nm or lower.

The optical modulator of the present invention is not limited as long as it applies modulation to the characteristic of light, and it may be an optical intensity modulator, or an optical phase modulator. The optical intensity modulator may be an optical amplitude modulator using a Mach-Zehnder optical waveguide. The optical phase modulator means one that applies phase modulation onto incident light and obtains a phase modulated signal from outgoing light.

EXAMPLES

Example 1

Figure 2:
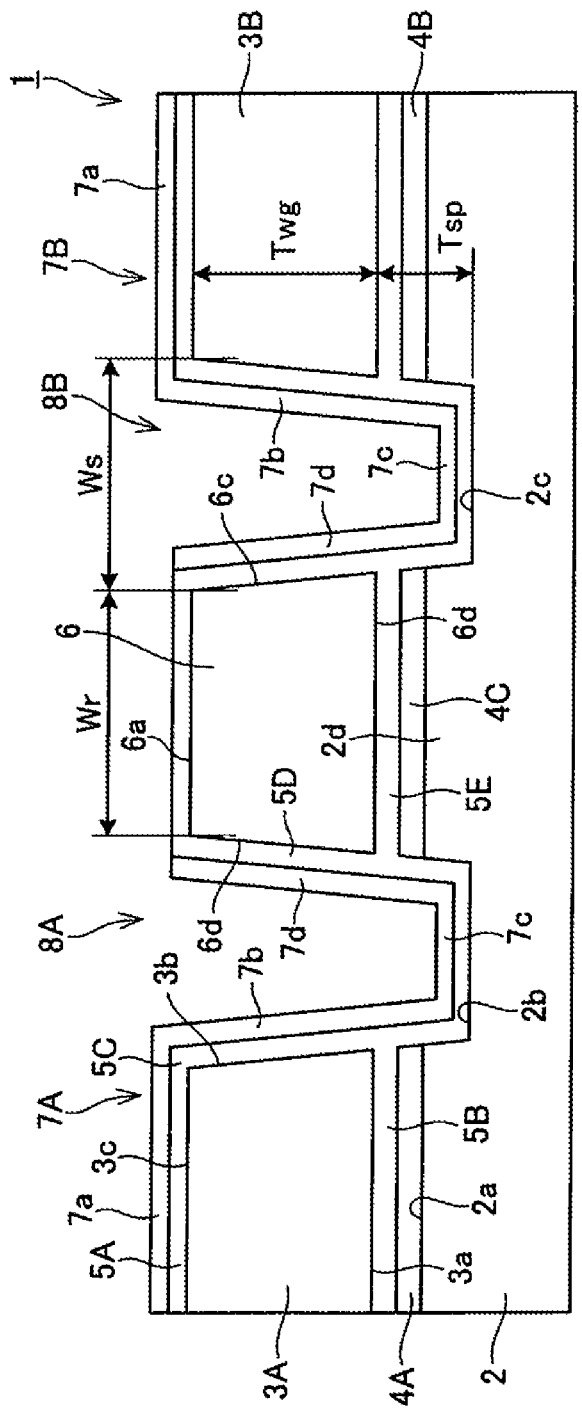
FIG. 2 is a cross sectional view schematically showing an essential portion of the optical modulation device shown in FIG. 1.

It was produced the device described referring to FIGS. 1 and 2 and its optical modulation characteristics were tested Specifically, a buffer layer of $SiO_2$ was formed in a thickness of 0.5 μm by sputtering on an upper face of a substrate of an x-plate of lithium niobate single crystal doped with 5% MgO having a thickness of 500 μm by sputtering. Then, the film-forming face of the x-plate of lithium niobate single crystal doped with 5% MgO was orientated downwardly and adhered onto a substrate of an x-plate 2 of non-doped lithium niobate single crystal and having a thickness of 2 mm, with a resin adhesive. Then, a surface of the substrate of MgO-doped lithium niobate single crystal was processed by grinding and lapping to a thickness of 70 μm. Thereafter, the substrate of MgO doped lithium niobate single crystal was ground using a dicing saw to form grooves 2b and 2c each having a depth of 100 μm so as to form a ridge part 6 having a width of 35 μm and a height of 70 μm. Further, a buffer layer made of $SiO_2$ was formed in a thickness of 0.5 μm, conductive films 7A, 7B are formed in the order of Ni, Cr and Au (thickness of 0.5 μm), and the $SiO_2$ buffer layer and the conductive films were patterned, by lithography, on the side face of the ridge waveguide, on the bottom faces of the ridge grooves and on the side faces and upper faces of the side ridges in both of the outsides to produce a phase-modulation device 1 shown in FIGS. 1 and 2.

Then, the device was cut with a dicing saw into chips each having a width of 3 mm and a length of 10 mm, and the chips were subjected to optical polishing at the end faces. Further, the phase modulation device was optically connected to a GI fiber having a core size of 50 μm with an UV curable resin. Finally, wire bonding was connected onto the electrode parts on the upper faces of the side parts in both outsides for the conduction with an outer circuit. The electrodes on the upper faces of the side ridge parts had a width of 1.2 mm in its either side (2.4 mm in both sides).

The followings are dimensions of the respective parts.

| | |
|---|---|
| Wr: | 35 μm |
| Ws: | 200 μm |
| Twg: | 70 μm |
| Tsp: | 30 μm |

The phase modulation device had an electrode length of 9.5 mm and a half wavelength voltage of 10V. 50 mW of light with a wavelength of 405 nm, 150 mW of light with a wavelength of 532 nm and 150 mW of light with a wavelength of 632 nm were made incident into the waveguide device to measure the modulation characteristics. Each light propagated in the optical waveguide in multi-mode propagation mode. For evaluating the modulation characteristics, a Mach-Zehnder interferometer system was constituted with fibers, its one arm was connected to the modulation device and its another arm was subjected to measurement of deviation of intensity modulated light without inserting anything. The modulation device was subjected to modulation at 1 kHz and ±10V, and it was proved that the deviation of bias point was reduced to 50 percent at each of the wavelengths. Further, twenty devices were subjected to the test, and the waveguides were not broken and the deviation of optical insertion loss was not observed.

Comparative Example 1

An optical modulation device was produced according to the same procedure as the Example 1, and its optical modulation characteristics were measured.

However, different from the Example 1, as to the first electrode, the electrode 7d on the side face 6b of the ridge part 6 and the conductive film 7c on the groove 2b were formed, and it was not formed on the side face 3b and upper face 3c of the side plate part 3A. Further, as to the second electrode, the electrode 7d on the side face 6c of the ridge part 6 and the conductive film 7c on the groove 2c were formed, and it was not formed on the side face 3b and the upper face 3c of the side plate part 38.

The phase modulation device had an electrode length of 9.5 mm and a half wavelength voltage of 10V. 50 mW of light with a wavelength of 405 nm, 150 mW of light with a wavelength of 532 nm and 150 mW of light with a wavelength of 632 nm were made incident into the waveguide device to measure the modulation characteristics. Each light propagated in the optical waveguide in multi-mode propagation mode. For evaluating the modulation characteristics, a Mach-Zehnder interferometer system was constituted with fibers, its one arm was connected to the modulation device and its another arm was subjected to measurement of deviation of intensity modulated light without inserting anything. The modulation device was subjected to modulation at 1 kHz and ±10V, and it was proved that the optical intensity was continuously and instantly deviated at each wavelength and the deviation of the bias point was proved to be 100 percent or more. Further, twenty devices were subjected to the test, and waveguides were broken and optical insertion loss was deteriorated by 2 dB in the two devices.

While specific preferred embodiments have been shown and described, the present invention is never limited by these specific embodiments, and can be carried out with various modifications and substitutions without departing from the spirit and scope of the claims of the present invention.

The invention claimed is:

1. An optical modulation device comprising:
   a supporting body comprising a first groove, a second groove, and a protrusion between said grooves;
   a ridge part comprising an electro-optic crystal and a channel type optical waveguide propagating light in multi mode formed therein;
   a first side plate part comprising an electro-optic crystal and formed in a first side of said ridge part;
   a second side plate part comprising an electro-optic crystal and formed in a second side of said ridge part;
   a first adhesive layer adhering said first side plate part and said supporting body;
   a second adhesive layer adhering said second side plate part and said supporting body;
   a third adhesive layer adhering said ridge part and said protrusion;
   a first electrode provided on a side face of said ridge part in a side of said first groove, said first groove, a side face of said first side plate part and an upper face of said first side plate part; and
   a second electrode provided on a side face of said ridge part in a side of said second groove, said second groove, a side face of said second side plate part and an upper face of said second side plate part;
   wherein said first electrode and said second electrode apply a modulation voltage modulating said light propagating in said channel type optical waveguide.

2. The optical modulation device of claim 1, wherein said ridge part has a thickness of 25 μm or larger and 150 μm or smaller.

3. The optical modulation device of claim 1, further comprising a buffer layer covering an upper face, said side face in said first groove side and said side face in said second groove side, and wherein said buffer layer is provided between said first electrode and side ridge part and between said second electrode and said ridge part.

4. The optical modulation device of claim 1, comprising a light source for flow cytometry.

* * * * *